(12) United States Patent
Virk et al.

(10) Patent No.: US 10,363,218 B1
(45) Date of Patent: Jul. 30, 2019

(54) SYNTHESIS OF PROBIOTIC NANOPARTICLES

(71) Applicant: KING SAUD UNIVERSITY, Riyadh (SA)

(72) Inventors: Promy Virk, Riyadh (SA); Manal Ahmed Gasmelseed Awad, Riyadh (SA); Amnah El-Enazy, Riyadh (SA); Awatif Ahmed Hendi, Riyadh (SA); Mai Abdelrahman Elobeid Wagealla, Riyadh (SA); Rabia Qindeel, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/239,277

(22) Filed: Jan. 3, 2019

(51) Int. Cl.
*A23L 33/135* (2016.01)
*A61K 9/16* (2006.01)
*A61P 39/06* (2006.01)
*A61K 35/741* (2015.01)

(52) U.S. Cl.
CPC .......... *A61K 9/1682* (2013.01); *A61K 35/741* (2013.01); *A61P 39/06* (2018.01)

(58) Field of Classification Search
CPC .... A01N 59/16; A01N 2300/00; A01N 25/04; A01N 25/08; A01N 25/34; A01N 63/02; A61K 31/20; A61K 2039/55511; A61K 2800/10; A61K 2800/412; A61K 2800/56; A61K 31/155; A61K 31/164; A61K 31/195; A61K 31/70; A61K 31/7088; A61K 35/74; A61K 39/00; A61K 39/39; A61K 47/18; A61K 47/183; A61K 47/26; A61K 47/646; A61K 8/0241; A61K 8/4973; A61K 8/60; A61K 8/735; A61K 8/737; A61K 8/86; A61K 9/0019; A61K 9/0031; A61K 9/0034; A61K 9/0043; A61K 9/14; A61K 9/145; A61K 9/51; A61K 9/5123; A61K 9/5192; A23L 33/135

See application file for complete search history.

(56) References Cited

U.S. PATENT DOCUMENTS

| 8,455,226 B2 | 6/2013 | De Windt |
| 2012/0114776 A1* | 5/2012 | Feher ...................... A61K 9/14 424/780 |

FOREIGN PATENT DOCUMENTS

CN 102978241 A 3/2013

OTHER PUBLICATIONS

Sathappart Shanthi et al., "Biosynthesis of silver nanoparticles using a probiotic Bacillus licheniformis Dahb1 and their antibiofilm activity and toxicity effects in Ceriodaphnia cornuta," Microbial Pathogenesis 93, pp. 70-77 (2016).

Yang Wang et al., "Antioxidant Properties of Probiotic Bacteria," Nutrients, 9, 521 (2017).

\* cited by examiner

*Primary Examiner* — Audrea B Coniglio
(74) *Attorney, Agent, or Firm* — Richard C. Litman

(57) ABSTRACT

A method of preparing probiotic nanoparticles can include dissolving formulated probiotics in methanol, spraying the methanol solution into boiling water under ultrasonic conditions to provide a sonicated solution, and stirring the sonicated solution to obtain probiotic nanoparticles. The probiotic nanoparticles may be cluster or rod-shaped. The probiotic nanoparticles may be administered to a subject to reduce oxidative stress or to treat diseases associated with oxidative stress.

7 Claims, 4 Drawing Sheets

SYNTHESIS OF PROBIOTIC NANOPARTICLES

BACKGROUND

1. Field

The disclosure of the present patent application relates to nanotechnology, and particularly to antioxidant probiotic nanoparticles.

2. Description of the Related Art

In materials science, nanomaterials have demonstrated unique, size and morphology based characteristics. Nanotechnology is an emerging field demonstrating significant potential for the development of new medicines. The most common methods of producing nanoparticles are chemical or mechanical, including ball milling, thermal quenching, precipitation techniques, and vapor deposition. However, these methods are often costly, and may result in toxic byproducts.

Biological approaches have also been developed, including use of probiotic microorganisms or plant extracts to synthesize nanoparticles, and in one instance probiotic nanoparticles. However, synthesis of nanoparticles using living microorganisms involves an expensive process requiring cell culture and multi-step purification. Further, the majority of these processes have focused on using the microorganisms to produce metal nanoparticles.

Probiotics are known to relieve oxidative stress, reducing or preventing damage to lipids, proteins, and DNA caused by oxygen radicals. Probiotic bacteria have been shown to have significant antioxidant effects both in vivo and in vitro. However, the safety and efficacy of long term administration of live probiotic microorganisms have yet to be established.

Thus, antioxidant probiotic nanoparticles solving the aforementioned problems are desired.

SUMMARY

A method of preparing probiotic nanoparticles can include dissolving formulated probiotics in methanol, spraying the methanol solution into boiling water under ultrasonic conditions to provide a sonicated solution, and stirring the sonicated solution to obtain probiotic nanoparticles. The probiotic nanoparticles may be cluster or rod-shaped. The probiotic may be a commercially available probiotic mixture of *Lactobacilli, Bifidobacterium* and *Saccharomyces*. The probiotic nanoparticles may be administered to a subject to reduce oxidative stress or to treat diseases associated with oxidative stress.

An embodiment of the present subject matter is directed to a pharmaceutical composition including the probiotic nanoparticle and a pharmaceutically acceptable carrier.

An embodiment of the present subject matter is directed to a method of making a pharmaceutical composition including mixing the probiotic nanoparticle under sterile conditions with a pharmaceutically acceptable carrier and preservatives, buffers, or propellants to create the pharmaceutical composition; and providing the pharmaceutical composition in a form suitable for daily, weekly, or monthly administration.

An embodiment of the present subject matter is directed to a method of treating cancer, including administering to a subject in need thereof a therapeutically effective amount of a pharmaceutical composition according to the present subject matter.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
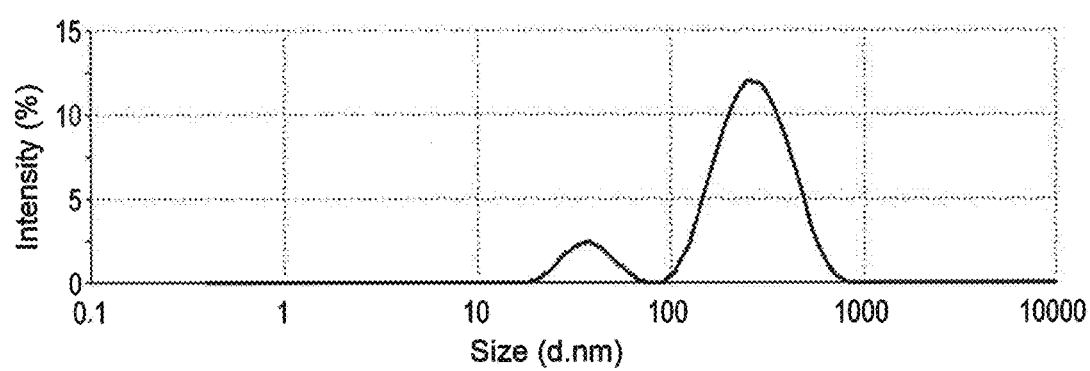
FIG. 1 depicts a graph of size distribution of the probiotic nanoparticles.

As used herein, a "subject" includes mammals, e.g., humans, dogs, cats, sheep, cows, rats, mice and the like.

As used herein, the term "about," when used to modify a numerical value, means within ten percent of that numerical value.

A method of preparing probiotic nanoparticles can include dissolving formulated probiotics in methanol, spraying the methanol solution into boiling water under ultrasonic conditions to provide a sonicated solution, and stirring the sonicated solution to obtain probiotic nanoparticles. The probiotic nanoparticles may be cluster or rod-shaped. The probiotic nanoparticles may be administered to a subject to reduce oxidative stress or to treat diseases associated with oxidative stress.

In an embodiment, the probiotic may be a commercially available probiotic mixture of *Lactobacilli, Bifidobacterium* and *Saccharomyces*. The commercially available probiotic may be PROTEXIN Balance probiotics, containing *Lactobacillus casei* PXN 37, *Lactobacillus rhermophils* PXN 54. *Streptococcus thermophiles* PXN 66, *Lactobacillus acidophilus* PXN 35, *Bifidobacterium breve* PXN 25, *Bifidobacterium longum* PXN 30, *Lactobacillus bulgaricus* PXN 39, fructooligosaccharide, and magnesium strearate.

In an embodiment, the methanol solution may be sprayed into the boiling water drop-wise with a controlled flow rate over five minutes under ultrasonic conditions. The controlled flow rate may be a flow rate of 0.2-0.4 ml/minute.

In an embodiment, the sonication may be for 60 minutes, and the stirring may be at 200-800 rpm at room temperature for about 20 to 30 minutes.

An embodiment of the present subject matter is directed to a pharmaceutical composition comprising the probiotic nanoparticles and a pharmaceutically acceptable carrier.

An embodiment of the present subject matter is directed to a method of making a pharmaceutical composition including mixing the probiotic nanoparticles with a pharmaceutically acceptable carrier. For example, the method of making a pharmaceutical composition can include mixing the probiotic nanoparticles under sterile conditions with a pharmaceutically acceptable carrier with preservatives, buffers, and/or propellants to create the pharmaceutical composition.

An embodiment of the present subject matter is directed to a pharmaceutical composition including the probiotic nanoparticles. To prepare the pharmaceutical composition, the probiotic nanoparticles, as the active ingredient, are intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by inhalation or insufflation. The active compound can be mixed under sterile conditions with a pharmaceutically acceptable carrier and, if required, any needed preservatives, buffers, or propellants. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose. A therapeutically effective amount of the probiotic nanoparticles or an amount effective to treat a disease, such as a disease associated with oxidative damage, may be determined initially from the Examples described herein and adjusted for specific targeted diseases using routine methods.

The antioxidant probiotic nanoparticles can be administered to a subject in need thereof. For example, the antioxidant probiotic nanoparticles can be used to treat a subject suffering from a disease associated with oxidative damage. The disease can be cancer or other diseases associated with oxidative damage.

An embodiment of the present subject matter is directed to a method of treating cancer, comprising administering to a subject in need thereof a therapeutically effective amount of the pharmaceutical composition according to the present subject matter.

The antioxidant probiotic nanoparticles or pharmaceutical compositions thereof can be administered to a subject by any suitable route. For example, the compositions can be administered orally (including bucally and sublingually), nasally, rectally, intracisternally, intra vaginally, intraperitoneally, topically, transdermally (as by powders, ointments, or drops), and/or parenterally. As used herein, "parenteral" administration refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation may also be contemplated, including, for example, embedding a composition of the disclosure in the body such as, for example, in a tissue, in the abdominal cavity, under the splenic capsule, brain, or in the cornea.

Accordingly, the route of administration can include intranasal administration, oral administration, inhalation administration, subcutaneous administration, transdermal administration, intradermal administration, intra-arterial administration with or without occlusion, intracranial administration, intraventricular administration, intravenous administration, buccal administration, intraperitoneal administration, intraocular administration, intramuscular administration, implantation administration, topical administration, intratumor administration, and/or central venous administration.

The following examples illustrate the present teachings.

Example 1

Characterizing the Probiotic Nanoparticles

Figure 2A:
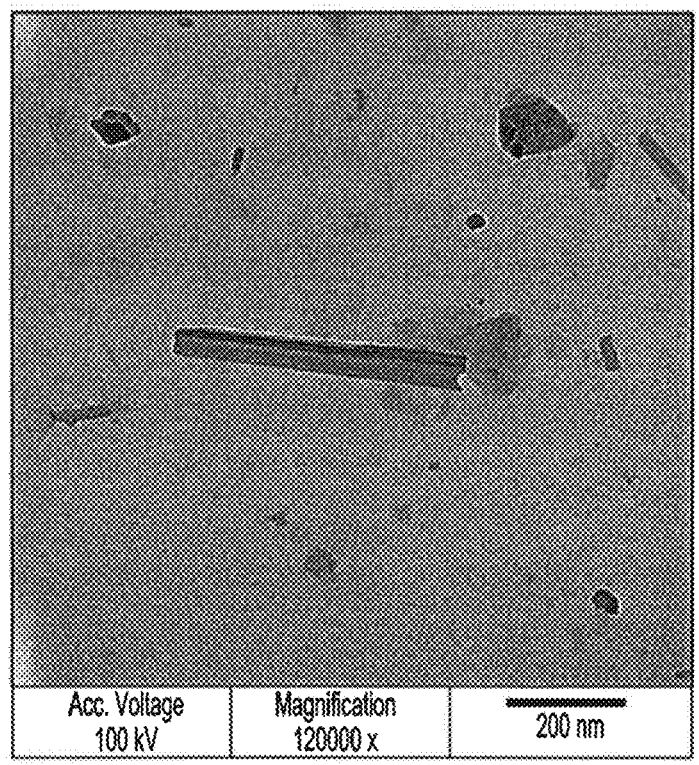
FIG. 2A depicts a transmission electron micrograph of the probiotic nanoparticles.
Figure 2B:
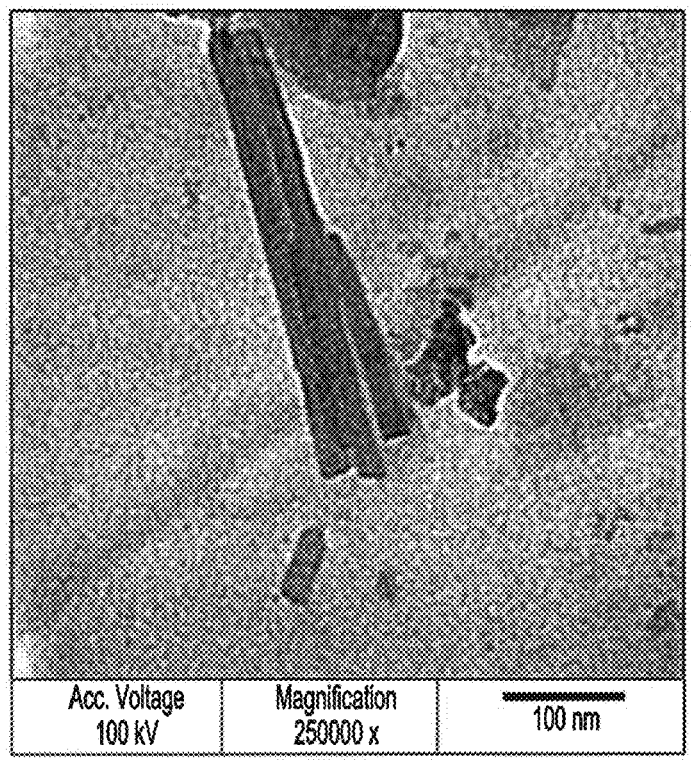
FIG. 2B depicts a transmission electron micrograph of the probiotic nanoparticles.

Probiotic nanoparticles were fabricated and tested to confirm size, dispersity, and shape of the resulting probiotic nanoparticles. The contents of a capsule containing 50-100 mg PROTEXIN Balance probiotics were dissolved in methanol (20-25 ml) to form a first solution. The first solution (1-2 ml) was then sprayed into boiling water (50-70 ml) dropwise with a flow rate of 0.2-0.4 ml min. in five minutes under ultrasonic conditions to form a second solution. The second solution was sonicated for sixty minutes, and stirred at 200 to 800 rpm at room temperature for about 20-30 minutes to produce the probiotic nanoparticles. The probiotic nanoparticles were then tested for size, dispersity, and shape. A Zetasizer was used to measure dynamic light scattering of the probiotic nanoparticles, identifying two contiguous peaks with a mean particle size of 166.2 nm and a poly dispersity index of 0.504. (FIG. 1) As shown in FIGS. 2A and 2B, transmission electron micrographs of the probiotic nanoparticles confirmed the presence of cluster and rod shaped nanoparticles.

Example 2

Effect of Probiotic Nanoparticles on Malondialdehyde Levels

The effect of the probiotic nanoparticles on malondialdehyde (MDA) levels was assessed in a Cadmium-induced oxidative stress model using male Wistar rats. Adult male Wistar rats (n=60), weighing 150-10 g, were procured from the Animal 1-louse Facility at King Saud University, Riyadh. The rats were acclimated to laboratory conditions of 22±2° C. in metabolic cages (6 rats/cage) and maintained under a 12 hour light/dark cycle. Rats were fed commercial diet and given tap water ad libitum. After 7 days of acclimatization, rates were randomly assigned into five groups of 6 rats each. Each group was then replicated, for a total of ten groups. Rats were gavaged with doses of various compositions, depending upon their groups. Control rats were given physiological saline, while treatment groups (Group 1-Group V) were given cadmium chloride (70 ppm in saline) alone, cadmium chloride (70 ppm) and the commercially available probiotic (1 ml containing $5 \times 10^9$ colony forming units in saline), cadmium chloride (70 ppm) and the probiotic nanoparticles (1 ml) in saline, or the probiotic nanoparticles (1 ml) alone.

Figure 3A:
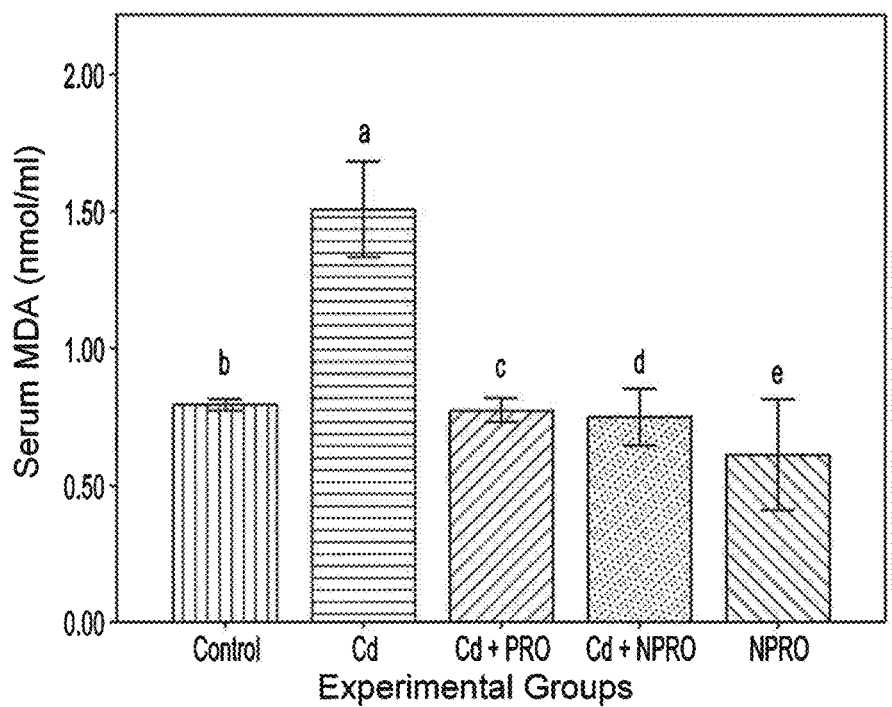
FIG. 3A depicts a graph of serum malondialdehyde levels in a cadmium-induced oxidative stress model.

As shown in FIG. 3A, serum MDA levels were significantly ($p \geq 0.05$) higher in the group administered cadmium alone (Cd, 1.507±0.1959 nmol/ml), in comparison to the control (Control, 0.7960±0.0242 6 nmol/ml). Treatment with probiotic (Cd+Pro, 0.7762±0.04838 nmol/ml) and the probiotic nanoparticles (Cd+NPro, 0.7516±0.11645 nmol/ml) significantly (p≤0.05) reduced the MDA levels in comparison to the group exposed to cadmium only. The MDA levels from the group exposed to the probiotic nanoparticles only (NPro) were not significantly different from the control group.

Example 3

Effect of Probiotic Nanoparticles on Glutathione Levels

The effect of the probiotic nanoparticles on glutathione (GSH) levels was assessed in a cadmium-induced oxidative stress model using male Wistar rats. Control rats were untreated, while treatment groups included administration of cadmium alone, administration of cadmium and the commercially available probiotic, administration of cadmium and the probiotic nanoparticles, and administration of the probiotic nanoparticles alone.

Figure 3B:
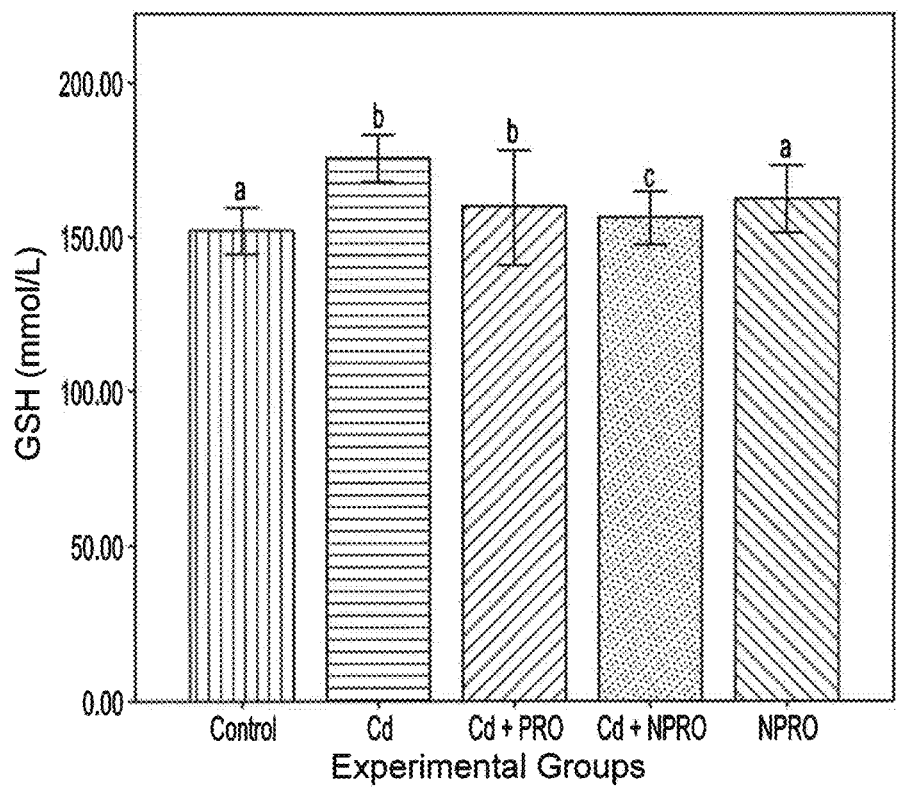
FIG. 3B depicts a graph of liver glutathione levels in a cadmium-induced oxidative stress model.

As shown in FIG. 3B, GSH levels in the liver were significantly (p≥0.05) higher in the group exposed to cadmium only (Cd, 175.3968±6.1389 mmol/L), in comparison to the control group (Control, 151.969±6.0682 mmol/L). Treatment with the probiotic (Cd+Pro) did not show a significant effect on GSH levels. However, treatment with the probiotic nanoparticles (Cd+NPro, 162.514±8.977 mmol/L) significantly (p≥0.05) reduced GSH levels in the liver in comparison to the group exposed to cadmium alone (Cd, 175.3968±6.1389 mmol/L). The GSH levels in the group exposed to probiotic nanoparticles alone (NPro) were not significantly different from the control group.

Example 4

Effect of Probiotic Nanoparticles on 8-hydroxy-20-deoxyguanosine Levels

The effect of the probiotic nanoparticles on 8-hydroxy-20-deoxyguanosine (8-OHdG) levels was assessed in a cadmium-induced oxidative stress model using male Wistar rats. Control rats were untreated, while treatment groups were given cadmium alone, cadmium and the commercially available probiotic, cadmium and the probiotic nanoparticles, or probiotic nanoparticles alone.

Figure 4:
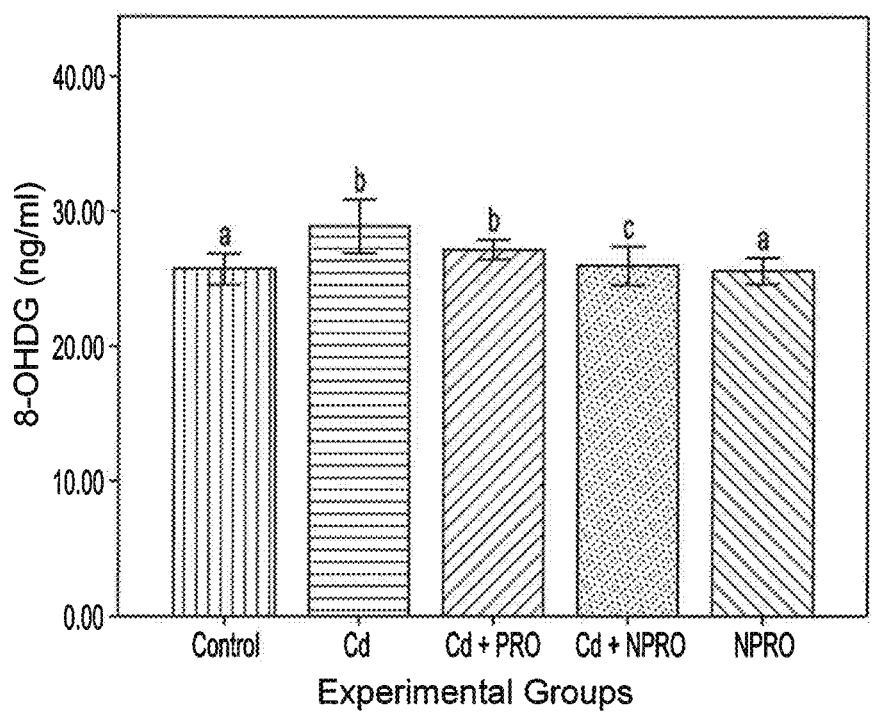
FIG. 4 depicts a graph of serum 8-hydroxy-20-deoxyguanosine levels in a cadmium-induced oxidative stress model.

As shown in FIG. 4, 8-OHdG levels in serum were significantly (p≥0.05) higher in the group exposed to cadmium alone (Cd, 28.883±1.582 ng/ml), in comparison to the control group (Control, 25.741±0.927 ng/ml). In the cadmium exposed groups, treatment with probiotic alone (Cd+Pro, 27.1994±0.582263 ng/ml) did not show a significant detectable effect on 8-OHDG levels. However, treatment with probiotic nanoparticles (Cd+NPro, 25.633±0.7795 ng/ml) significantly (p≥0.05) reduced the 8-OHDG levels in comparison to the group exposed to cadmium alone (Cd, 28.883±1.582 ng/ml). The 8-OHDG serum levels in the group exposed to probiotic nanoparticles alone (NPro) were not significantly different from the control group.

Example 5

Effect of Probiotic Nanoparticles on Metallothionein Levels

The effect of the probiotic nanoparticles on Metallothionein (MT) levels was assessed in a cadmium-induced oxidative stress model using male Wistar rats. Control rats were untreated, while treatment groups were given cadmium alone, cadmium and the commercially available probiotic, cadmium and the probiotic nanoparticles, and probiotic nanoparticles alone.

Figure 5:
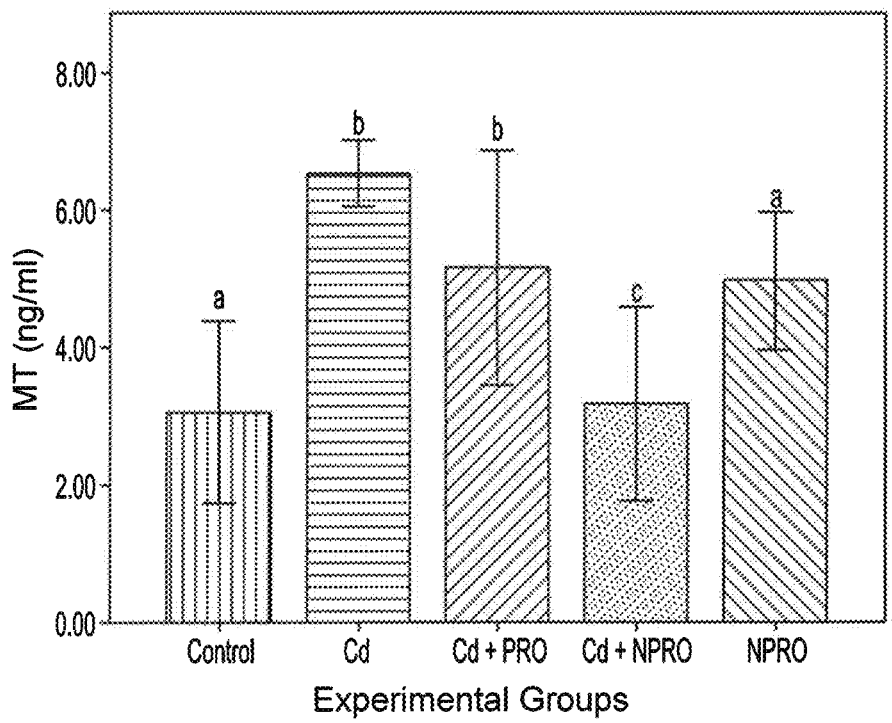
FIG. 5 depicts a graph of liver metallothionein levels in a cadmium-induced oxidative stress model.

As shown in FIG. 5, MT levels in liver were significantly (p≥0.05) enhanced in the group exposed to cadmium alone (Cd, 6.532±0.3864 ng/ml), in comparison to the control (Control, 3.061±1.0676 ng/ml). Within the treated groups, treatment with probiotic nanoparticles (Cd+Pro) significantly (p≥0.05) reduced MT levels (3.1768±1.13015 ng/ml) in comparison to the group exposed to cadmium alone. Treatment with the probiotic (Cd+Pro) did not have significant effect on the MT levels. Thus, treatment with the probiotic nanoparticles (Cd+NPro) was significantly (p≥0.05) more effective in reducing MT levels in the liver in comparison to the group treated with probiotics (Cd+Pro). MT levels from the group exposed to nanoprobiotic only (NPro) were not significantly different from the control group.

It is to be understood that the probiotic nanoparticles are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. An method of fabricating a probiotic nanoparticle, comprising:
   (a) dissolving a probiotic in methanol to form a first solution;
   (b) spraying the first solution into boiling water at a controlled flow rate under ultrasonic conditions to form a sonicated solution; and
   (c) stirring the sonicated solution to provide the probiotic nanoparticle.

2. The method of fabricating a probiotic nanoparticle of claim 1, wherein the controlled flow rate is 0.2 ml/min-0.4 ml/min for five minutes.

3. The method of fabricating a probiotic nanoparticle of claim 1, wherein the ultrasonic conditions comprise sonicating for 60 minutes.

4. The method of fabricating a probiotic nanoparticle of claim 1, wherein the stirring is performed at a speed of about 200 rpm to about 800 rpm at room temperature for about 20 to about 30 minutes.

5. Probiotic nanoparticles prepared according to the method of claim 1.

6. The probiotic nanoparticles according to claim 5, wherein the nanoparticles have a mean particle size of 166.2 nm.

7. A pharmaceutical composition, comprising the probiotic nanoparticles according to claim 5 and a pharmaceutically acceptable carrier.

* * * * *